United States Patent [19]

Ghahramani

[11] 4,260,226
[45] Apr. 7, 1981

[54] EYE DEPTH PERCEPTION TESTING APPARATUS

[76] Inventor: Bahador Ghahramani, 752 Bourbon Ave., Baton Rouge, La. 70803

[21] Appl. No.: 72,120

[22] Filed: Sep. 4, 1979

[51] Int. Cl.$^3$ ............................ A61B 3/08; A61B 3/02
[52] U.S. Cl. ........................................... 351/3; 351/33; 351/37
[58] Field of Search .............................. 351/3, 33, 37

[56] References Cited

U.S. PATENT DOCUMENTS 4,035,066  7/1977  Slomski ..................................... 351/3

Primary Examiner—John K. Corbin
Assistant Examiner—Rodney B. Bovernick
Attorney, Agent, or Firm—Llewellyn A. Proctor

[57] ABSTRACT

An improved, and more objective, eye depth perception testing apparatus wherein the eyes of a patient are tested by observing test specimens, posts or pegs of varying colors, varying shapes, varying lateral spacings, and at different lighting conditions. The apparatus, in its preferred aspects embodies a housing upon a floor or ceiling of which is provided parallel tracks within which is mounted a pair of carriers which carry transverse holders which carry a pair of pegs the lateral spacing of which can be adjusted to different widths. These pegs, the movement of which is controlled by the patient, being tested, are exchangeable, vary in color and cross-sectional shape. The walls of the apparatus are mirrored, and the inside of the apparatus is provided with a source of light which can be varied over a range of illuminations of varying intensity. The mirrors disperse the light, and eliminate reference sources, or points, this creating greater objectivity in the testing.

10 Claims, 6 Drawing Figures

EYE DEPTH PERCEPTION TESTING APPARATUS

The eyes of man, and those of all vertebrates, are end organs which react to light and conveys to the brain the sensation of vision. The eye may be considered a light refracting apparatus, and may be advantageously compared to a camera. The photographic lens is represented by the refracting media, the cornea and the lens; the photosensitive film corresponds to the retina, the innermost of the tunics of the eye. Rays of light coming from the exterior are distributed in the eye according to the laws of geometrical optics. In man, the rays are collected and refracted by the cornea; some light proceeding to the lens where additional refraction takes place. Accommodation of the lens focuses the refracted rays of light on the retina, to form a real image that is far smaller than the object viewed, and the object is symmetrically inverted. This signal is transmitted via various nerve cells to the brain where it is interpreted as a visual image.

Various diseases of the eyes, or parts of the eyes are known. Many other disorders are caused from physiological variations, these affecting the operation or functioning of the eye as an optical instrumentent, e.g., emmetropia, myopia, hyperopia and astigmatism. These disorders and others are also often caused by hereditary factors, though they can also be caused by disease. Some disorders of the eyes, moreover, are caused by physical injury; and others are believed psychological. Whatever the cause, however, there are profound differences between the eyes of different persons to perceive depth, or spacial relationships between objects located in a given field. Good depth perception among people engaged in certain occupations, trades or professions is essential, e.g., airline pilots, crane operators, bus drivers, etc. Consequently, since good eye depth perception is essential in such occupations, testing devices, or methods for determining the quality of the eye depth perception of individuals is also essential for use in the selection of individuals for certain types of employment.

It is known to test eye depth perception by the use of an instrument, or device wherein two elongated posts, or pegs, of equal length are vertically mounted upon carriers which are slidably movable within elongated parallel tracks, the carriers being controlled and moved either forward or backward in unison within the tracks by a person, or patient, whose eyes are being tested for depth perception. The pegs are of similar shape, and each is vertically mounted on its respective carrier in a fixed lateral position, one peg relative to the other. The pegs cannot be moved inwardly, or outwardly one member relative to the other. The pegs are without color; and are black. The pegs are uniformly round in cross-section. Light from a random source falls upon the pegs during the testing, and the structure within which the pegs are mounted is usually a walled box-like structure, like into a black box.

Whereas this type of device has been employed for testing eye depth perception for several decades its use in eye depth perception testing leaves much to be desired. The device is deficient in that it does not take into account various possible eye deficiencies which may impact upon depth perception, i.e. differing eye reactions to different colors, different distances between the objects being viewed and contrasted, different shapes (cross-sectional shapes), different illuminations and the like. It is, however, highly desirable in testing the depth perception of eyes to test the ability of the eyes to perceive objects of different color, objects spaced apart at different preselected distances, objects of different cross-sectional shape, and to view such objects at different illuminations, and conditions as may be caused to change due to cloudiness, time of day, fog and the like. It is also important to provide testing apparatus which more objectively tests the vision of a patient for eye depth perception by suppression, or elimination of judgment factors.

It is, accordingly, the primary objective of the present invention to provide new and improved eye depth perception testing apparatus which will obviate these and other disadvantages of prior art apparatus.

A particular object is to provide eye depth perception testing apparatus which tests the ability of a patient to perceive the different spacial condition of objects of different shape, different lighting conditions, and the like.

These objects and others are achieved in accordance with the present invention which embodies apparatus for testing the eye depth perception of a patient, the apparatus including the usual combination of a housing, a pair of carriers, each carrying perpendicularly oriented pegs mounted within spaced parallel aligned elongate slots located upon a horizontally disposed planar member constituting a portion of the housing, and a looped line handled by the patient for testing the ability of his eyes to perceive depth, the carriers, or pegs, being moved by his pulling the carriers within the elongated slots to effect, to the extent possible, side-by-side alignment of the vertically oriented pegs; and additionally, such novel features as a pair of holders, each of which is mounted upon a carrier, transversely or laterally relative to the line of movement of the carriers, or direction of the slots, these providing means for vertically mounting a pair of pegs of varying colors and cross-sectional configurations preselected distances apart; mirrored walls located inside the housing, these at least partially surrounding the carriers, or pegs, the reflecting faces of which are directed inwardly; the pegs being illuminated by a light source of adjustable intensity which emits light into said mirrored portion of the housing.

In its more preferred aspects, the apparatus embodies a housing, including upper and lower compartments, the upper compartment including vertically oriented walls, viz. a windowed front wall, a rear wall and parallel aligned relatively long side walls which adjoin the front and rear walls, and a hinged lid, preferably a lid hinged to the top of the rear wall. The lower compartment includes vertically oriented walls which may be extensions of the walls of the upper compartment, a floor and a transparent upper panel, preferably a frosted glass panel which separates the upper and lower compartments.

The lid is provided with a pair of spaced parallel aligned elongate slots, in-line with the length wise direction of the lid, these providing tracks within which the carriers with their respective holders, and projecting pegs, can be unilaterally moved in either of two directions, and the land areas between and alongside the slots are panelled with mirrors, the reflecting surfaces of which are faced inwardly into the housing.

The rear wall and inside side walls of the upper compartment are also panelled with mirrors, the reflective surfaces of which are faced inwardly. Preferably, transversely movable mirrors are mounted inside the side walls of the upper compartment, with their reflective surfaces faced inwardly. Suitably, a mechanism is mounted with the housing by virtue of which the mirrors can be moved in unison inwardly or outwardly. A light source of adjustable intensity is located within the lower compartment of the housing, and light can be directed through the transparent panel which separates the upper and lower compartments of the housing.

Use of mirrors prevents light absorption by the walls of the housing. The more uniform light intensity, at any given moment in time, eliminates landmarks of reference sources and consequently suppresses the judgment factor such that the testing becomes more objective. Depth perception is tested for different colors, and shapes; and at different light intensities. By different lateral peg spacings, flaws in a patients vision can be detected and viewing angle changes can be effected by movement of the walls.

Preferred eye depth perception testing apparatus, and the principle of its operation, will be described and the invention more fully understood by reference to the following more detailed description, and drawings. In the description reference is made to the drawings. Similar numbers are used to represent similar parts or components in the different figures, and subscripts are generally used with a given whole number, or letter, to designate a plurality of generally analogous parts or components. Where the subscripts are dropped from numbers in a general discussion, subsequent to their introduction, the reference is intended to apply in a generic sense.

Figure 1:
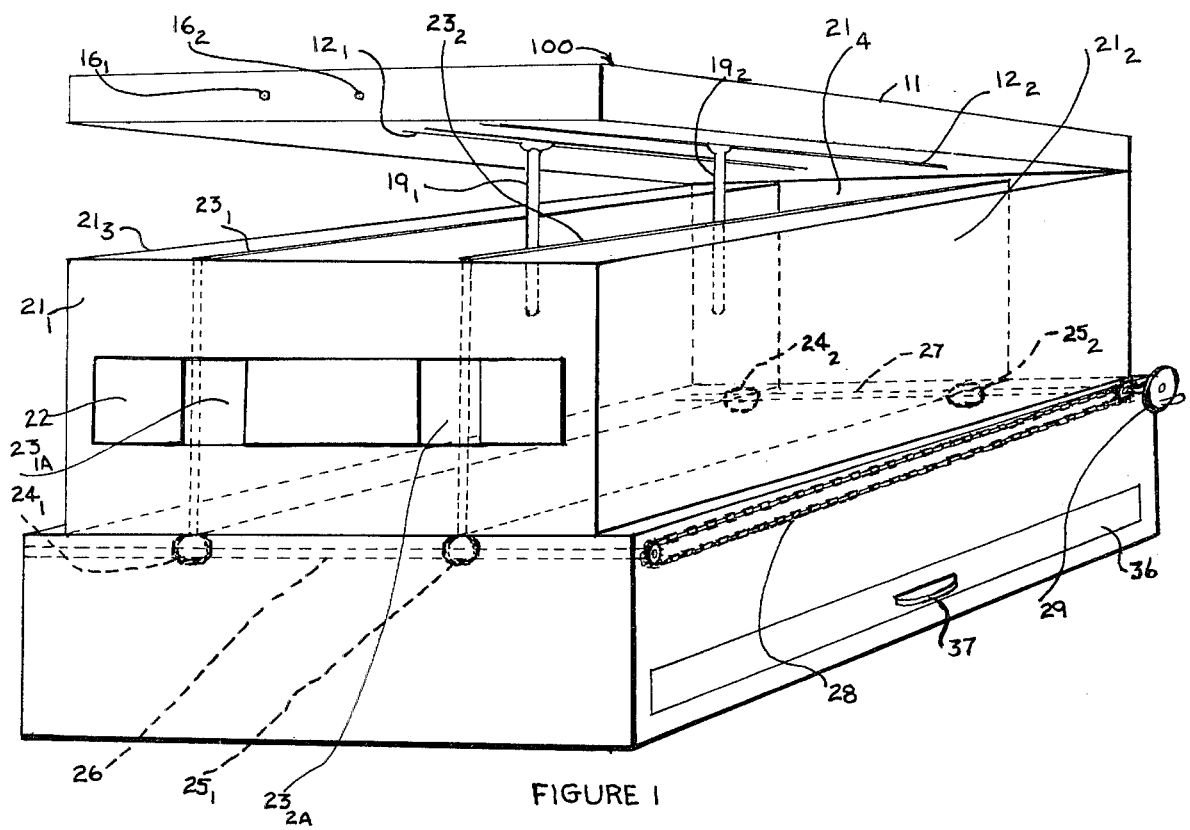
FIG. 1 is a perspective view taken from the front, and toward one side of the apparatus showing a housing, and a cover, or lid thereof in slightly raised position to show the interior in better perspective.

Referring to the figures, particularly to FIG. 1, there is shown an eye depth perception testing apparatus 100. In general, the apparatus 100 is constituted of a compartmented housing, inclusive of upper and lower compartments. The upper compartment is provided with an upwardly lifting hinged cover, or lid 11 (slightly lifted in FIG. 1) provided with hinges 9 within which is contained a pair of parallel elongated slots $12_1$, $12_2$ in each of which is carried a movable bar, $14_1$, $14_2$ and from each of which a peg $19_1$, $19_2$ is vertically projected when the lid 11 is in horizontally oriented and closed position. The upper compartment is also provided with enclosing vertically oriented walls, a windowed front wall $21_1$, a back wall $21_4$ parallel thereto, and parallel side walls $21_2$, $21_3$ which are adjoined to the front and rear walls. The faces of the back wall $21_4$ and lid 11 are covered with mirrors, and a pair of movably adjustable inwardly faced mirrors $23_1$, $23_2$ are located alongside the side walls $21_2$, $21_3$. The upper and lower compartments are separated one from the other by a frosted glass panel 32. The lower compartment accommodates a light source near its upward side, suitably a lighting panel upon which a plurality of light bulbs 33 are arrayed, the panel of light bulbs 33 being capable of emitting light of adjustable intensity upwardly through the frosted glass panel 32 which separates the upper and lower compartments. The lower compartment can also provide storage space below the light panel, and it houses suitable circuitry for adjusting the light intensity.

Figure 2:
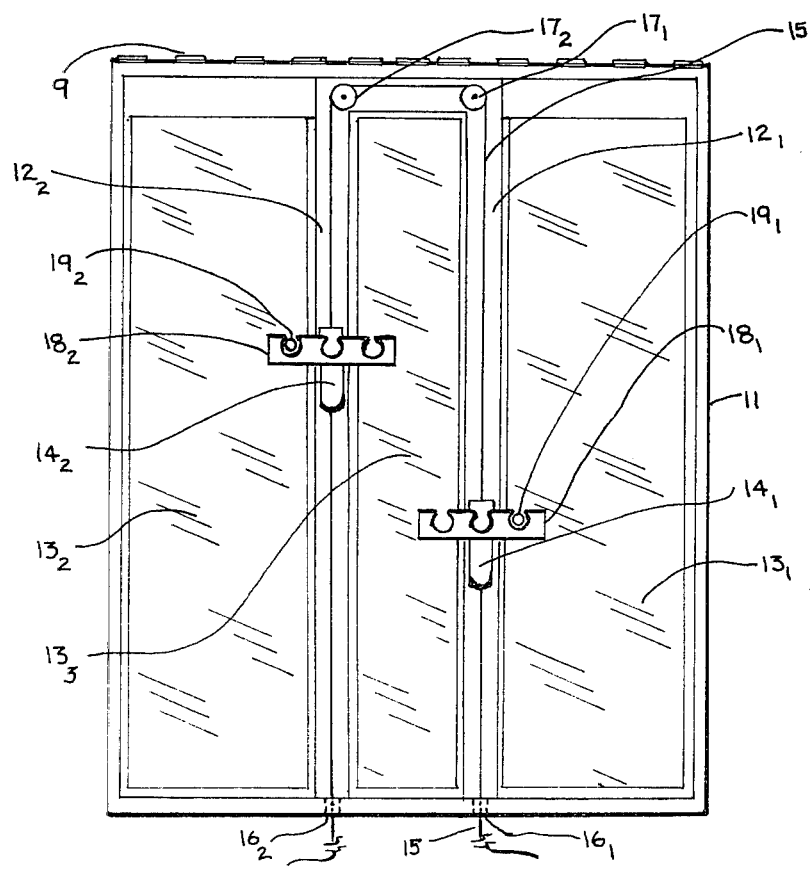
FIG. 2 depicts a view taken from the underside of the lid, or cover.
Figure 3:
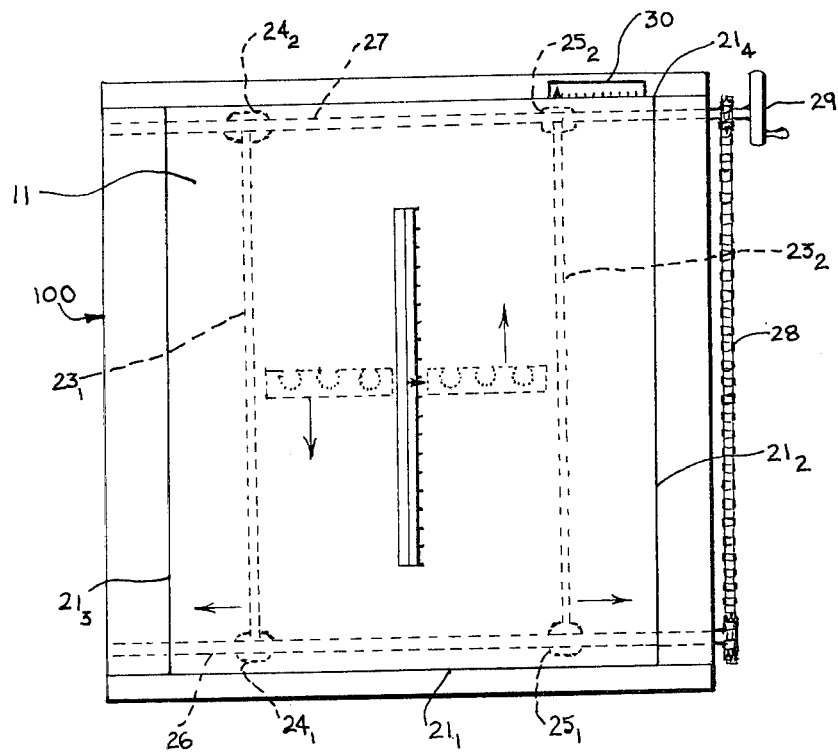
FIG. 3 depicts a top view of the apparatus, with the lid, or cover, in closed position.

The features of the hinged cover, or lid 11 are best shown by direct reference to FIGS. 2 and 3. Referring first to FIG. 2, it will be observed that the inwardly faced side of the lid 11 is provided with a pair of parallelly aligned elongate slots $12_1$, $12_2$ which substantially transverse the entire length of the lid 11. The land surface on each side, and between the elongate slots 12, is panelled with mirrors $13_1$, $13_2$, $13_3$. Each slot 12 carries an elongate bar $14_1$, $14_2$, and each bar 14 is appended to and movable with the loop of rope, or line 15. The forward ends of line 15 are adjoined to the forward end of elongate bars $14_1$, $14_2$ and extend through a pair of openings $16_1$, $16_2$ in the forward end of lid 11, and the rearward portion of the loop 15 is extended from the rearward ends of bars $14_1$, $14_2$, to which they are affixed, around a pair of spaced apart sheaves or pulleys $17_1$, $17_2$ which guides the loop 15 in a circular path. Each bar $14_1$, $14_2$ is provided with a slotted elongate holder $18_1$, $18_2$, laterally affixed to each, within the individual slots of which changable pegs $19_1$, $19_2$ can be placed and transversely spaced apart one from the other in preselected disposition, as desired. It will be quite apparent that a pull on a forward end of the line 15 will cause movement of one of the bars 14 in one direction, while the other is moved in the opposite direction. In other words, a pull on the segment of line 15 attached to the forward end of bar $14_2$ will move bar $14_2$ forward toward opening $16_2$ of the lid 11, while simultaneously the bar $14_1$ will move rearwardly. Conversely, a pull on the segment of line 15 attached to the forward end of bar $14_1$ will move bar $14_1$ toward the opening $16_1$ of lid 11, while the bar $14_2$ will move rearwardly toward the hinged side of the lid 11. Quite clearly also, the transverse distance between the pegs 19 is narrowed by moving the pegs $19_1$, $19_2$ to the more inward slots of slotted elongate holders 18; and conversely, the transverse distance between the pegs 10 is increased by movement of the pegs $19_1$, $19_2$ to the more outward slots of slotted elongate holders 18.

It will be observed by reference to FIG. 3 that the relative distance between the elongate bars $14_1$, $14_2$ can be read from a scale located on the upper face of the lid 11. When on the one hand, for example, the elongate bars $14_1$, $14_2$ are precisely transverse one member relative to the other the scale will read "zero". When, on the other hand, the elongate bars $14_1$, $14_2$ are not precisely transversely aligned, the distance of each from the zero position will be equal and opposite.

The forward wall $21_1$ of the upper compartment of the housing is provided with a window 22, through which pegs $19_1$, $19_2$ can be viewed. The fixed parallel side walls $21_2$, $21_3$ and rear wall $21_4$, on the upper side of which the rearward edge of the lid 11 is hinged, provide a box like structure of parallelogram shape which rests atop the lower compartment which forms a base. The inside rear wall $21_4$ of the upper compartment is panneled, and the face thereof completely covered with an inwardly reflecting mirror. Two vertically erected mirrors $23_1$, $23_2$, or mirrored walls the reflecting surface of which are faced inwardly, are each parallelly aligned upon an inside face of the outer side walls $21_2$, $21_3$, and each is movable toward or away from an outer side wall, respectively.

The forward edges of each of the mirrors $23_1$, $23_2$ are provided with blocks $23_{1a}$, $23_{2a}$ which fit and are slidably movable, like tongue and groove, within the viewing slot 22 located within front wall $21_1$. These blocks $23_{1a}$, $23_{2a}$, with paired threaded connections $24_1$, $24_2$ and $25_1$, $25_2$ (which are threadably engaged to threaded shafts 26, 27, respectively) located on the forward and rearward lower edges of the mirrors $23_1$, $23_2$ provide stability for the vertical orientation of, as well as a means for lateral movement of said mirrors 23.

Figure 4:
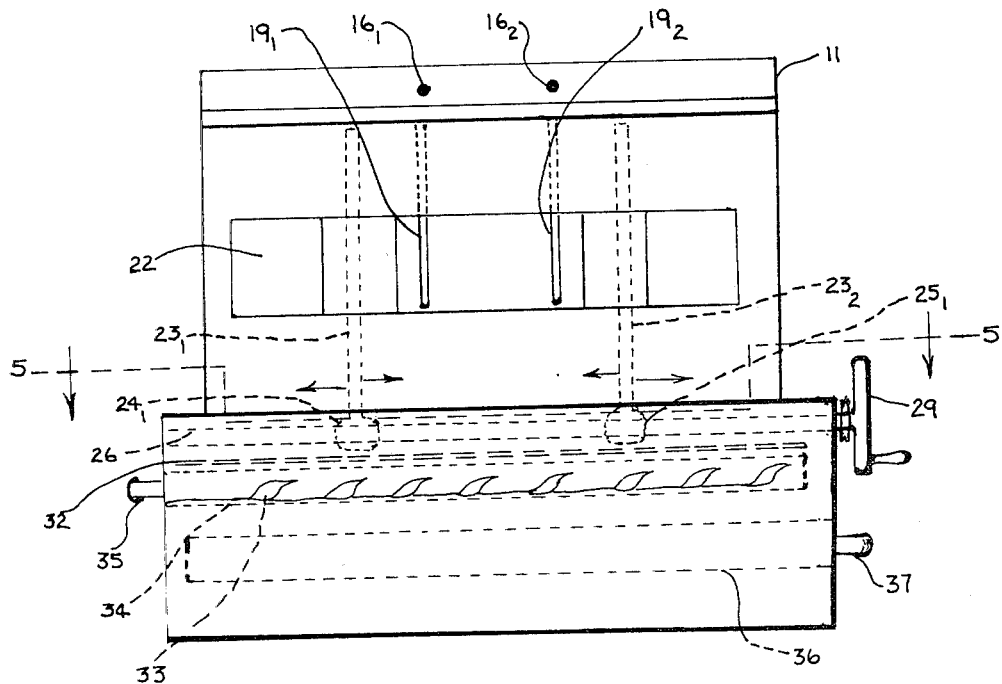
FIG. 4 depicts a front elevation view of the apparatus.
Figure 5:
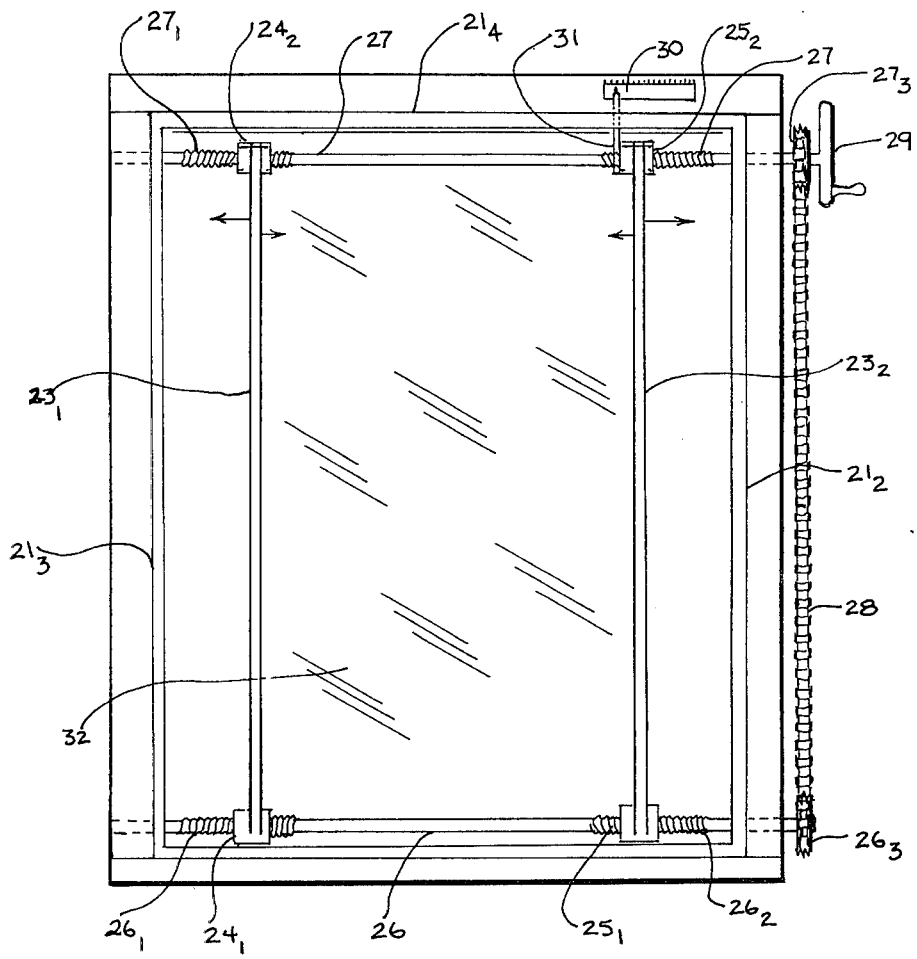
FIG. 5 depicts a sectional view showing in plan a view taken along lines 5—5 in the direction of the arrows.

The manner in which lateral movement is imparted to mirrors $23_1$, $23_2$ is best shown by reference to FIG. 4 and 5, particularly the latter. As suggested, paired threaded connections $24_1$, $24_2$ and $25_1$, $25_2$, which carry mirrors $23_1$, $23_2$, respectively, are threadably engaged to shafts 26, 27 which are journelled transversely within the housing, just above the frosted glass panel which separates the lower compartment from the upper compartment. Each end of a shaft 26, 27 is threaded and the threaded ends $26_1$, $26_2$ and $27_1$, $27_2$ of each shaft 26, 27, respectively, is of equal and opposite pitch. The threads $26_1$, $27_1$ and $26_2$, $27_2$, respectively, are also of equal pitch. The shafts 26, 27 are geared together via a drive chain 28 which is meshed with gears $26_3$, $27_3$ affixed to the ends of shafts 26, 27, respectively; and the mirrors $23_1$, $23_2$ are moved in unison transversely outwardly one away from another, or inwardly one toward the other, by rotation of a handled gear crank wheel 29. A scale 30 which measures the relative distance between mirrors $23_1$, $23_2$ is located outside the wall $21_4$, and atop an upper face of the lower compartment of the housing. A pointer 31, a portion of scale 30, is thus attached to the threaded connection $25_2$ of mirror $23_2$ and is extended outwardly through a port in the rear wall, and is movable in unison with mirrors $23_1$, $23_2$ to provide a convenient scale 30 for measuring the relative distance apart of mirror $23_1$, $23_2$. If desired, the terminal end of the pointer 31 can be extended vertically and the scale 30 located on vertically oriented wall $21_4$.

A light source for illuminating the interior of the upper compartment of the housing is essential, and suitably a plurality of light bulbs 33 contained in an electrical circuit are arranged across a suitable horizontally oriented panel located below the frosted glass 32. In a preferred arrangement, shown by reference to FIG. 4, the circuit of light bulb 33 is arrayed, with the bulbs 33 spaced apart, upon the floor of a drawer 34 located within the upper side of the lower compartment of the housing. The drawer 34 is conveniently provided with a handle 35 so that the drawer 34 can be slid outwardly for servicing, and replacement of said bulbs 33. The electric circuit is conventional in all respects, and the circuit includes a rheostat (not shown) by virtue of which the lumination from the bulbs 33 can be increased, or the bulbs 33 dimmed. A drawer 36, located below the drawer 34, provides a convenient storage space for various spare pieces of equipment, e.g. pegs 19, bulbs 33, etc. A floor constitutes the very bottom of the lower compartment.

Figure 6:
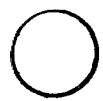
FIG. 6 depicts preferred sub-assemblies, in cross-section, for use in the apparatus.
Figure 6:
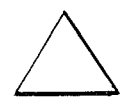
Figure 6:
Figure 6:

As earlier suggested, a feature of this invention is that the pegs 19 of this invention can be of various colors, e.g. red, yellow, blue, green, black, white and various shades thereof. And, as shown by reference to FIG. 6, the posts 19 are of various cross-sectional configurations, e.g. round, triangular, square, rectangular and the like.

In operation and use of the eye depth perception Apparatus 100, the first step is to determine the color, and cross-sectional configuration of the pegs 19 that are to be used, and the desired spacing of a pair of the selected pegs 19 of similar color and cross-section. This is determined by tests on the patients eyes. The mirrors $23_1$, $23_2$ are then adjusted to the desired spacing, the lid 11 of the housing is closed, and the rheostat is then adjusted to provide the desired illumination from bulbs 33. The patient, while viewing from a measured distance the pegs 19 through the elongated opening 22 within front wall 21, then operates the two ends of line 16 with his two hands and attempts, to the best of his ability, to align the pegs 19 as closely as possible in a side-to-side relationship. The ability, or inability, of the patient to accomplish this task constitutes a measure of his eyes to perceive depth.

It is apparent that various substitutions, modifications and changes, such as in the location, or in the absolute or relative dimensions of the parts, materials used and the like, can be made without departing the spirit and scope of the invention as will be apparent to those skilled in the art.

Having described the invention, what is claimed is:

1. In apparatus for testing the eye depth perception of a patient which includes the combination of a housing, inclusive of a planar, horizontally oriented member on which there is provided a pair of spaced parallelly aligned elongate slots, a pair of carriers, each of which is mounted and movable within an elongate slot, respectively, of said planar, horizontally oriented member, a pair of elongated pegs, of substantially equal length, each of which is mounted upon, and vertically projected from one of said carriers, respectively, and movable therewith within said elongate slots, respectively, a line shaped as a loop, two sides of which can be handled by the patient, these ends thereof being secured to the sides of the carriers faced toward the patient, while the other ends are secured to the opposite sides of the carriers and looped so that pulls by the patient on the side of the loop handled by the patient will cause unilateral movement of the carriers, in either direction, within the elongated slots, with consequent movement of the vertically projected elongate pegs to and from a separated side-by-side position to a more distant separation by movement of the pegs one away from the other, the improvement comprising a pair of holders, one each of which is transversely mounted upon a movable carrier, respectively, each providing a means for mounting a preselected distance apart pegs of varying color and cross-section, mirrored walls, at least partially surrounding said carriers, and pegs, the reflecting faces of which are directly inwardly, constituting a portion of said housing, a light source of adjustable intensity for emitting light into said housing whereby such an arrangement of said mirrored walls causes dispersing of said light and elimination of landmark points, thus creating greater objectivity in testing.

2. The apparatus of claim 1 wherein the planar, horizontally oriented member on which the elongate parallelly aligned pair of slots, carriers, peg holders and pegs are mounted is constituted of a hinged lid mounted atop the upper compartment of a housing which includes an enclosing rear wall, and windowed front wall, the inside faces of the hinged lid and rear wall are panelled with inwardly faced mirrors, a lower compartment in the housing contains the adjustable light emitting source, and the floor of the upper and lower compartments of the housing are separated by a transparent floor through which light from the emitting source can be passed.

3. The apparatus of claim 2 wherein transversely movable, vertically oriented mirrors, with their reflecting sides faced inwardly, are mounted alongside, inside, and parallel to said side walls.

4. The apparatus of claim 3 wherein the forward ends of the transversely movable, vertically oriented mirrors include projections which fit slidably within the window of said windowed front wall in a tongue and groove arrangement, and the lower front and rearward sides of each of said mirrors are threadably engaged with transversely aligned shafts the ends of each of which, respectively, are threaded with similar threads of equal and opposite pitch, the outer portions of the shafts are provided with fixed gears, and geared one to the other via a chain such that rotation of the chain in one direction moves the mirrors transversely in one direction, and rotation of the chain in the opposite direction moves the mirrors transversely in the opposite direction.

5. The apparatus of claim 2 wherein the light source is constituted of a circuit containing a plurality of light bulbs arrayed upon a panel beneath the partitioning transparent floor.

6. The apparatus of claim 5 wherein the floor panel which the circuit containing the plurality of light bulbs is arrayed, constitutes a drawer within the lower compartment of the housing.

7. The apparatus of claim 6 wherein a second drawer is located within the lower compartment of the housing, beneath the drawer on which the circuit containing the circuit with said plurality of light bulbs is arrayed.

8. An apparatus for testing the eye depth perception of a patient which includes, the combination comprising
a housing, including upper and lower compartments,
the upper compartment including vertically oriented walls, a windowed front wall, a rear wall, and parallel aligned side walls connect the windowed front wall and rear wall, and a hinged lid,
the lower compartment including vertically oriented walls, a floor, and a transparent upper panel which separates the upper and lower compartments,
a pair of spaced parallelly aligned elongated slots oriented along the length of, and located in the lid of said upper compartment, mirrors with their reflecting surfaces facing inwardly located on the land areas between said slots of the lid,
a pair of carriers, each mounted and movable within an elongate slot of said lid,
a pair of holders, one each of which is transversely mounted upon a movable carrier, each providing a means for mounting a preselected distance apart pegs of varying color and cross-section,
a pair of replacable elongated pegs of substantially equal length, each of which is mounted upon and downwardly vertically projected from a holder of said carriers when the lid is closed, and movable with said carriers within said elongate slots,
a looped line, two sides of which can be handled by the patient, the ends thereof being secured to the sides of the carriers facing the patient, while the other ends are secured to the opposite sides of the carriers and the mid-portion thereof looped over a pulley system contained at the rearward end of said lid such that pulls by the patient on the loop side handled by the patient will cause unilateral movement of the carriers, in either direction, within the elongated slots with consequent movement of the vertically projected pegs to and from a separated close side-by-side position to a more distant separation by movements of the pegs one away from the other,
a light source of adjustable intensity located within the lower compartment of the housing for directing light through the transparent upper panel in the lower compartment which separates the upper and lower compartments of the housing, and
transversely movable, vertically oriented mirrors, with their reflecting sides faced inwardly, mounted in the upper compartment alongside, inside and parallel to said side walls,
whereby said movable mirrors cause dispersing of said light and elimination of landmarks or reference sources or points, thus creating greater objectivity in testing.

9. The apparatus of claim 8 wherein the forward ends of the transversely movable, vertically oriented mirrors include projections which fit slidably within the window of said windowed front wall, and the lower front and rearward sides of each of said mirrors are threadably engaged with transversely aligned shafts the ends of which, respectively, are threaded with similar threads of equal and opposite pitch, and the shafts are geared together so that rotation of the shafts in one direction moves the mirrors transversely in one direction, and rotation of the shafts in the other direction moves the mirror transversely in the opposite direction.

10. The apparatus of claim 9 wherein the shafts are geared together via a chain and provided with a handle for movement of the chain with consequent rotation of the shafts.

* * * * *